US012697091B2

(12) United States Patent
Bourlion et al.

(10) Patent No.: US 12,697,091 B2
(45) Date of Patent: Aug. 4, 2026

(54) MEDICAL SYSTEM AND METHOD FOR LOCATING AN ENTRY POINT OF A SURGICAL INSTRUMENT IN AN ANATOMICAL STRUCTURE AND FOR IDENTIFYING A TRAJECTORY OF THE SURGICAL INSTRUMENT IN THE ANATOMICAL STRUCTURE, AND ASSEMBLY COMPRISING SUCH A MEDICAL SYSTEM AND A SURGICAL INSTRUMENT

(71) Applicant: SPINEGUARD, Saint Mande (FR)

(72) Inventors: Maurice Bourlion, Rive de Gier (FR); Randal R. Betz, Ocean City, NJ (US); Ciaran Bolger, Dublin (IE); Andrè Kaelin, Collonge-Bellerive (CH); Larry T. Khoo, Los Angeles, CA (US); John I. Williams, Fort Wayne, IN (US); Hee-Kit Wong, Singapore (SG)

(73) Assignee: SpineGuard, Vincennes (FR)

( * ) Notice: Subject to any disclaimer, the term of this patent is extended or adjusted under 35 U.S.C. 154(b) by 902 days.

(21) Appl. No.: 15/115,988

(22) PCT Filed: Feb. 3, 2015

(86) PCT No.: PCT/FR2015/050241
§ 371 (c)(1),
(2) Date: Aug. 16, 2023

(87) PCT Pub. No.: WO2015/114282
PCT Pub. Date: Aug. 6, 2015

(65) Prior Publication Data
US 2024/0016471 A1     Jan. 18, 2024

(30) Foreign Application Priority Data

Feb. 3, 2014     (FR) ...................................... 14 00305

(51) Int. Cl.
| | | |
|---|---|---|
| *A61B 8/08* | (2006.01) | |
| *A61B 17/16* | (2006.01) | |
| *A61B 90/00* | (2016.01) | |

(52) U.S. Cl.
CPC .......... *A61B 8/0875* (2013.01); *A61B 8/0841* (2013.01); *A61B 17/1671* (2013.01); *A61B 90/37* (2016.02)

(58) Field of Classification Search
CPC .............. A61B 17/1671; A61B 18/148; A61B 2017/00261; A61B 2018/0044; A61B 17/1757
See application file for complete search history.

(56) References Cited

U.S. PATENT DOCUMENTS

| | | |
|---|---|---|
| 5,334,205 A | 8/1994 | Cain |
| 6,337,994 B1 | 1/2002 | Stoianovici et al. |
| (Continued) | | |

FOREIGN PATENT DOCUMENTS

| | | |
|---|---|---|
| CN | 1929789 A | 3/2007 |
| CN | 103948412 A | 7/2014 |
| (Continued) | | |

OTHER PUBLICATIONS

Yamada, M., Moriya, H., Iino, T., Kasai, Y., Sudo, A., & Uchida, A. (2012). Ultrasonic measurement of bone thickness for spinal surgery. IEEE transactions on ultrasonics, ferroelectrics, and frequency control, 59(9), 2077-2088. (Year: 2012).*

(Continued)

*Primary Examiner* — Keith M Raymond
*Assistant Examiner* — Johnathan Maynard
(74) *Attorney, Agent, or Firm* — Greenberg Traurig, LLP; Christopher C. Bolten; Albert K. Heng

(57)     ABSTRACT

The invention relates to a medical system comprising a tool including: a body; a location measurement device adapted to (Continued)

emit an ultrasound location signal and receive a reflected location signal; a location processing device adapted to compare each of the echoes of the reflected location signal to a pre-determined location threshold, emit an information signal if no target location echo corresponding to the interface between first and second anatomical structures has been identified within an analysis time window, the target location echo having an amplitude that exceeds the location threshold.

13 Claims, 6 Drawing Sheets

(56)                References Cited

U.S. PATENT DOCUMENTS

| | | |
|---|---|---|
| 6,470,207 B1 | 10/2002 | Simon et al. |
| 6,635,062 B2 | 10/2003 | Ray, III et al. |
| 6,796,985 B2 | 9/2004 | Bolger et al. |
| 7,580,743 B2 | 8/2009 | Bourlion et al. |
| 8,092,457 B2 | 1/2012 | Oettinger et al. |
| 8,118,594 B2 | 2/2012 | Pernot et al. |
| 8,221,428 B2 | 7/2012 | Trieu |
| 8,361,152 B2 | 1/2013 | McCormack et al. |
| 8,419,746 B2 | 4/2013 | Bourlion et al. |
| 8,486,119 B2 | 7/2013 | Bourlion |
| 8,634,897 B2 | 1/2014 | Simon et al. |
| 8,795,285 B2 | 8/2014 | Kwon |
| 8,939,979 B2 | 1/2015 | Del et al. |
| 9,066,751 B2 | 6/2015 | Sasso |
| 9,119,732 B2 | 9/2015 | Schifano et al. |
| 9,204,830 B2 | 12/2015 | Zand et al. |
| 9,538,935 B2 | 1/2017 | Bourlion et al. |
| 9,855,060 B2 | 1/2018 | Ardel et al. |
| 9,901,283 B2 | 2/2018 | Bourlion et al. |
| 9,937,009 B2 | 4/2018 | Schroeder et al. |
| 10,064,630 B2 | 9/2018 | Forman et al. |
| 10,092,300 B2 | 10/2018 | Del et al. |
| 10,149,729 B2 | 12/2018 | Smaby et al. |
| 10,624,572 B2 | 4/2020 | Bourlion et al. |
| 10,987,113 B2 | 4/2021 | Mcginley et al. |
| 11,000,292 B2 | 5/2021 | Mcginley |
| 11,058,436 B2 | 7/2021 | Mcginley et al. |
| 11,083,469 B2 | 8/2021 | Del et al. |
| 11,291,381 B2 | 4/2022 | Bourlion et al. |
| 11,344,372 B2 | 5/2022 | Bourlion et al. |
| 11,399,902 B2 | 8/2022 | Bourlion et al. |
| 11,789,177 B2 | 10/2023 | Hokstad |
| 11,903,591 B2 | 2/2024 | Chen et al. |
| 12,161,348 B2 | 12/2024 | Lorian et al. |
| 12,213,683 B2 | 2/2025 | Del et al. |
| 12,458,367 B2 | 11/2025 | Chandanson et al. |
| 2002/0120197 A1* | 8/2002 | Kleffner .................. A61B 17/16 |
| | | 600/459 |
| 2003/0078495 A1 | 4/2003 | Goodwin |
| 2003/0187348 A1* | 10/2003 | Goodwin ........... A61B 17/1671 |
| | | 606/130 |
| 2005/0116673 A1 | 6/2005 | Carl et al. |
| 2005/0119660 A1* | 6/2005 | Bourlion ............ A61B 17/1626 |
| | | 606/80 |
| 2006/0241628 A1 | 10/2006 | Parak |
| 2006/0258951 A1* | 11/2006 | Bleich ................. A61B 17/8861 |
| | | 600/546 |
| 2007/0218420 A1 | 9/2007 | Syribeys |
| 2007/0239187 A1 | 10/2007 | Brunnett et al. |
| 2008/0086140 A1 | 4/2008 | Wolf |
| 2008/0262526 A1 | 10/2008 | Neubardt et al. |
| 2009/0157059 A1 | 6/2009 | Allen et al. |
| 2010/0024981 A1 | 2/2010 | Wallace et al. |
| 2010/0286694 A1 | 11/2010 | Rio et al. |
| 2011/0015649 A1 | 1/2011 | Anvari et al. |
| 2012/0046668 A1 | 2/2012 | Gantes |
| 2012/0296213 A1* | 11/2012 | Mauldin, Jr. ............ A61B 8/42 |
| | | 600/443 |

| | | |
|---|---|---|
| 2013/0085413 A1 | 4/2013 | Tsamir et al. |
| 2013/0085505 A1 | 4/2013 | Markey et al. |
| 2013/0152746 A1 | 6/2013 | Kerboul et al. |
| 2013/0172902 A1 | 7/2013 | Lightcap et al. |
| 2013/0296734 A1 | 11/2013 | Bourlion et al. |
| 2014/0094808 A1 | 4/2014 | Herndon |
| 2014/0276002 A1 | 9/2014 | West et al. |
| 2014/0276839 A1 | 9/2014 | Forman et al. |
| 2014/0276950 A1 | 9/2014 | Smaby et al. |
| 2014/0324044 A1 | 10/2014 | Haufe et al. |
| 2015/0066030 A1 | 3/2015 | Mcginley et al. |
| 2015/0148176 A1 | 5/2015 | Schroeder et al. |
| 2015/0196306 A1 | 7/2015 | Del et al. |
| 2015/0366624 A1 | 12/2015 | Kostrzewski et al. |
| 2016/0012582 A1* | 1/2016 | Mauldin, Jr. ........ A61B 8/5269 |
| | | 600/449 |
| 2016/0074123 A1 | 3/2016 | Bly et al. |
| 2016/0106392 A1* | 4/2016 | Manbachi ................ A61B 8/54 |
| | | 600/447 |
| 2016/0302871 A1 | 10/2016 | Gregerson et al. |
| 2016/0361069 A1 | 12/2016 | Ardel et al. |
| 2016/0361070 A1 | 12/2016 | Ardel et al. |
| 2017/0007199 A1 | 1/2017 | Bourlion et al. |
| 2017/0056116 A1 | 3/2017 | Kostrzewski |
| 2017/0100822 A1 | 4/2017 | Cutler |
| 2017/0360493 A1 | 12/2017 | Zucker et al. |
| 2018/0042514 A1 | 2/2018 | Verard et al. |
| 2018/0098714 A1 | 4/2018 | Bourlion et al. |
| 2018/0177556 A1 | 6/2018 | Noonan |
| 2018/0242985 A1 | 8/2018 | Vipperman et al. |
| 2019/0175886 A1 | 6/2019 | Abdelwahed et al. |
| 2019/0201011 A1 | 7/2019 | Del et al. |
| 2019/0388173 A1 | 12/2019 | Pak et al. |
| 2020/0324408 A1 | 10/2020 | Bourlion et al. |
| 2020/0337782 A1 | 10/2020 | Glassman et al. |
| 2021/0068905 A1 | 3/2021 | Quaid et al. |
| 2021/0282862 A1 | 9/2021 | Bourlion et al. |
| 2021/0298795 A1 | 9/2021 | Bowling et al. |
| 2022/0022891 A1 | 1/2022 | Del et al. |
| 2022/0104901 A1 | 4/2022 | Lawrie |
| 2022/0168048 A1 | 6/2022 | Shoham et al. |
| 2022/0175455 A1 | 6/2022 | Ungi et al. |
| 2022/0175462 A1 | 6/2022 | Turgeman et al. |
| 2022/0218421 A1 | 7/2022 | Junio et al. |
| 2022/0233250 A1 | 7/2022 | Bette et al. |
| 2022/0361896 A1 | 11/2022 | Bette et al. |
| 2022/0361897 A1 | 11/2022 | Chen et al. |
| 2022/0409214 A1 | 12/2022 | Lorian et al. |
| 2023/0088846 A1 | 3/2023 | Laing et al. |
| 2023/0095197 A1 | 3/2023 | Chandanson et al. |
| 2023/0134461 A1 | 5/2023 | Casey et al. |
| 2024/0237994 A1 | 7/2024 | Chandanson et al. |

FOREIGN PATENT DOCUMENTS

| | | | |
|---|---|---|---|
| CN | 107921554 A | 4/2018 | |
| CN | 110882037 A | 3/2020 | |
| CN | 118251181 A | 6/2024 | |
| DE | 102010042012 A1 * | 4/2012 | ......... A61B 17/7092 |
| DE | 102011083360 A1 * | 3/2013 | ............. G01S 15/88 |
| EP | 1474046 A1 | 11/2004 | |
| EP | 3319539 A1 | 5/2018 | |
| EP | 3525696 A1 | 8/2019 | |
| EP | 3761870 A1 | 1/2021 | |
| EP | 3883491 A1 | 9/2021 | |
| FR | 2795624 A1 | 1/2001 | |
| FR | 3034643 A1 | 10/2016 | |
| JP | 2005525150 A | 8/2005 | |
| JP | 2016518878 A | 6/2016 | |
| WO | WO 03/068076 A1 | 8/2003 | |
| WO | WO-2014146090 A1 | 9/2014 | |
| WO | WO-2015006296 A1 | 1/2015 | |
| WO | WO-2016043676 A1 | 3/2016 | |
| WO | WO-2016162634 A1 | 10/2016 | |
| WO | WO-2016199152 A1 | 12/2016 | |
| WO | WO-2019002578 A1 | 1/2019 | |
| WO | WO-2019081850 A1 | 5/2019 | |
| WO | WO-2019110119 A1 | 6/2019 | |
| WO | WO-2020000038 A1 | 1/2020 | |

(56)                References Cited

FOREIGN PATENT DOCUMENTS

| WO | WO-2020097481 A1 | 5/2020 |
| WO | WO-2021046247 A1 | 3/2021 |
| WO | WO-2021111439 A1 | 6/2021 |
| WO | WO-2021178706 A1 | 9/2021 |
| WO | WO-2022170185 A1 | 8/2022 |

OTHER PUBLICATIONS

Manbachi, A., Cobbold, R. S., & Ginsberg, H. J. (2014). Guided pedicle screw insertion: techniques and training. The Spine Journal, 14(1), 165-179. (Year: 2014).*

Aly, A. H., Ginsberg, H. J., & Cobbold, R. S. (2011). On ultrasound imaging for guided screw insertion in spinal fusion surgery. Ultrasound in medicine & biology, 37(4), 651-664. (Year: 2011).*

Mujagic, M., Ginsberg, H. J., & Cobbold, R. S. (2008). Development of a method for ultrasound-guided placement of pedicle screws. IEEE transactions on ultrasonics, ferroelectrics, and frequency control, 55(6), 1267-1276. (Year: 2008).*

Chang, J. H., Raphael, D. T., Zhang, Y. P., & Shung, K. K. (2011). Proof of concept: in vitro measurement of correlation between radiodensity and ultrasound echo response of ovine vertebral bodies. Ultrasonics, 51(3), 253-257. (Year: 2011).*

Raphael, D. T., Chang, J. H., Zhang, Y. P., Kudija, D., Chen, T. C., & Shung, K. K. (2010). A-Mode ultrasound guidance for pedicle screw advancement in ovine vertebral bodies. The Spine Journal, 10(5), 422-432. (Year: 2010).*

Lou, E., Zhang, C., Le, L., Hill, D., Raso, J., Moreau, M., . . . & Hedden, D. (2010). Using ultrasound to guide the insertion of pedicle screws during scoliosis surgery. In Research into Spinal Deformities 7 (pp. 44-48). IOS Press. (Year: 2010).*

Kantelhardt, S. R., Larsen, J., Bockermann, V., Schillinger, W., Giese, A., & Rohde, V. (2009). Intraosseous ultrasonography to determine the accuracy of drill hole positioning prior to the placement of pedicle screws: an experimental study. Journal of Neurosurgery: Spine, 11(6), 673-680. (Year: 2009).*

Kantelhardt, S. R., Bock, H. C., Siam, L., Larsen, J., Burger, R., Schillinger, W., . . . & Giese, A. (2010). Intra-osseous ultrasound for pedicle screw positioning in the subaxial cervical spine: an experimental study. Acta neurochirurgica, 152(4), 655-661. (Year: 2010).*

Kantelhardt, S. R., Bock, C. H., Larsen, J., Bockermann, V., Schillinger, W., Rohde, V., & Giese, A. (2009). Intraosseous ultrasound in the placement of pedicle screws in the lumbar spine. Spine, 34(4), 400-407. (Year: 2009).*

International Search Report Application No. PCT/FR2015/050241 reported on May 4, 2015.

Balmer, et al., Characterization of the Electrical Conductivity of Bone and Its Correlation to Osseous Structure, Scientific Reports, 8:8601 (2018).

International Search Report & Written Opinion dated Aug. 31, 2022 in Int'l PCT Patent Appl. Serial No. PCT/EP2022/061868.

International Search Report & Written Opinion dated Oct. 1, 2024 in Int'l PCT Patent Appl. Serial No. PCT/EP2024/017206.

International Search Report & Written Opinion dated Dec. 15, 2022 in Int'l PCT Patent Appl. No. PCT/IB2022/059201.

International Search Report and Written Opinion for PCT Application No. PCT/IL2020/051241, mailed Mar. 22, 2021, 13 pages.

International Search Report and Written Opinion for PCT Application No. PCT/IL2022/050585, mailed Nov. 3, 2022, 15 pages.

Int'l Search Report & Written Opinion dated Jan. 7, 2019 in Int'l PCT Patent Appl. Serial No. PCT/FR2018/052640.

* cited by examiner

MEDICAL SYSTEM AND METHOD FOR LOCATING AN ENTRY POINT OF A SURGICAL INSTRUMENT IN AN ANATOMICAL STRUCTURE AND FOR IDENTIFYING A TRAJECTORY OF THE SURGICAL INSTRUMENT IN THE ANATOMICAL STRUCTURE, AND ASSEMBLY COMPRISING SUCH A MEDICAL SYSTEM AND A SURGICAL INSTRUMENT

CROSS-REFERENCE TO RELATED APPLICATION

This Application is a 35 USC § 371 US National Stage filing of International Application No. PCT/FR2015/050241 filed on Feb. 3, 2015, and claims priority under the Paris Convention to French Patent Application No. 14 00305 filed on Feb. 3, 2014.

FIELD OF THE DISCLOSURE

The invention relates to a medical system and method for locating an entry point of a surgical instrument into an anatomical structure and for identifying a path of the surgical instrument in the anatomical structure, as well as an assembly comprising such a medical system and a surgical instrument.

BACKGROUND OF THE DISCLOSURE

The invention relates more particularly to a medical system for locating an entry point of a surgical instrument into a first anatomical structure of a body part of a patient, and for identifying a path of the surgical instrument in the anatomical structure, the body part further comprising a second anatomical structure having a portion that covers the first anatomical structure.

The invention applies in particular to the field of orthopedic surgery, for the placement of an implant in a bone structure serving as the first anatomical structure, in order to reconstruct the bone structure, consolidate a damaged body part or restore a falling anatomical function.

To reduce the risk of damage to functional tissue near the bone structure, such as nervous system tissue, and to ensure a firm and durable retention of the implant in the bone structure, it is important to accurately position the surgical instrument comprising the implant or comprising a suitable tool for shaping sites on the bone structure, such as fastening holes, to which the implant is fixed. The importance of accurately positioning the surgical instrument is even greater when attaching an implant in the pedicle of a spinal vertebra, immediately adjacent to the functional tissues of the spinal cord, nerve endings, and vascular structures.

The surgical instrument described in patent application WO 03/068076 and marketed as PediGuard® is known to efficiently and safely provide real-time monitoring of the insertion of an implant or of a tool suitable for shaping the sites where the implant is to be fixed.

However, precise positioning of the surgical instrument assumes an accurate determination of the entry point of the surgical instrument into the bone structure. But this bone structure, usually covered by a soft tissue structure, serving as the second anatomical structure, in the approaches said to be minimally invasive or percutaneous, is not directly visible to the practitioner responsible for placing the implant.

To determine the entry point into the bone structure and more particularly into the vertebral pedicle, experienced practitioners may resort to palpation.

Such a determination, which is empirical, is difficult to generalize and reproduce. Moreover, it does not provide all the precision required for an intervention on a body part as sensitive as the spinal column.

To improve accuracy in positioning the entry point, X-ray medical imaging techniques are generally used. The X-ray images are obtained either during surgery (one common example is the use of C-arm fluoroscopy) or before surgery by a scanner with intraoperative registration (for navigation).

However, such a determination exposes the patient and the staff responsible for capturing the images used for determining the entry point into the bone structure, to excessive amounts of harmful radiation.

Other medical systems, such as those described in documents US 2002/0120197 and US 200310078495, use ultrasonic techniques to determine the positioning of a surgical instrument or implant. These medical systems comprise:

a measurement device adapted for receiving, at a plurality of sites, reflected signals corresponding to a reflection of a portion of ultrasonic signals on inhomogeneities and interfaces between different anatomical structures of different acoustic impedances, and a processing device connected to the measurement device, for characterizing the different anatomical structures.

The ultrasound technique implemented by these medical systems provides for processing a set of echoes of varying amplitudes at each site in order to determine a type and geometry of the anatomical structures.

These medical systems are time-consuming and complex to use, however, for the positioning of a surgical instrument.

The invention aims to overcome the problems mentioned above.

SUMMARY OF THE DISCLOSURE

For this purpose, in a first aspect, the invention provides a medical system for locating an entry point of a surgical instrument into a first anatomical structure of a body part of a patient, and for identifying a path of the surgical instrument in the first anatomical structure, the body part further comprising a second anatomical structure having a portion that covers the first anatomical structure, the first and second anatomical structures respectively having surfaces in contact defining at least one interface, the first anatomical structure having an external surface, the second anatomical structure having an internal surface in contact with the external surface of the first anatomical structure, and an external surface opposite the first anatomical structure, the first and second anatomical structures respectively having first and second acoustic impedances, the first acoustic impedance being greater than the second acoustic impedance, the medical system comprising a tool including:

a body extending along a central axis between opposite proximal and distal ends and having an external surface, a location measurement device adapted for, in at least one site of the external surface of the first anatomical structure:

emitting from the distal end of the body at least one ultrasound location signal adapted to propagate in the first anatomical structure and to be at least partially reflected at the interface between the first and second anatomical structures, and

3 receiving at least one reflected location signal corresponding to a reflection of a portion of the ultrasound location signal, the reflected location signal being in the form of a plurality of echoes of amplitudes that vary over time, a location processing device connected to the location measurement device, wherein the location processing device is adapted for comparing, at each site, each of the echoes of the reflected location signal to a defined location threshold, emitting an information signal if no target location echo corresponding to the interface between the first and second anatomical structures has been identified within an analysis time window, the target location echo having an amplitude which exceeds the location threshold.

The invention thus, through a non-invasive technique without any harmful radiation, allows the practitioner not only to locate the entry point into the first anatomical structure where the surgical instrument is to penetrate but also to identify the path of the surgical instrument. The location of the entry point and the identification of the appropriate path are based on the absence of detection of the interface between the first and second anatomical structures within the analysis time window, solely from the difference in acoustic impedance between the first and second anatomical structures and, for example, between the bone structure and soft tissue structure, the acoustic impedance of the bone structure being clearly higher than that of the soft tissue structure. The processing is based on a simple comparison of the echoes of the reflected location signal and the location threshold, carried out within a limited predetermined time, in order to characterize the disappearance of the ultrasound location signal in a thickness of the first anatomical structure that is deemed sufficient. Such a medical system thus provides an efficient and safe real-time determination of the entry point of the surgical instrument into the first anatomical structure and of the path of the surgical instrument.

The analysis time window may be defined by a starting point, such as the emission of the ultrasound location signal or the detection of a first target location echo, and a duration, in particular comprised between 1 μs and 100 μs.

To locate the entry point and to identify the path of the surgical instrument in a bone structure serving as the first anatomical structure, the body part further comprising a soft tissue structure serving as the second anatomical structure, the location measurement device may be adapted to emit an ultrasonic wave of a frequency between 100 kHz and 10 MHz.

The location measurement device may comprise at least one ultrasonic transducer arranged on the body, the body having an emission-reception surface in contact with the ultrasonic transducer and adapted for emitting the ultrasound location signal and for receiving the reflected location signal, the emission-reception surface being positioned at the distal end of the body on the external surface of the body.

In particular, the ultrasonic transducer may be arranged at a distance from the distal end of the body, the body having a transmission member adapted to transmit the ultrasound location signal and the reflected location signal, the transmission member being in contact with the ultrasonic transducer and providing the emission-reception surface.

In one embodiment, the tool may further comprise:
at least one first electrode having a first contact surface arranged at the distal end of the body on the external surface of the body so as to come into contact with the first anatomical structure,

at least one second electrode having a second contact surface arranged at the distal end of the body on the external surface of the body so as to come into contact with the first anatomical structure at a distance from the first contact surface,
a layer of electrically insulating material interposed between the first and second electrodes,
an electric measurement device adapted to measure continuously and in real time an electrical characteristic representative of the capacity of the first anatomical structure for conducting electric current between the first and second contact surfaces,
wherein the layer of electrically insulating material forms the transmission member, the emission-reception surface being arranged between the first and second contact surfaces.

The first electrode may be cylindrical and extend along the central axis, the second electrode may be annular and extend along the central axis around the first electrode, the layer of electrically insulating material being annular and extending along the central axis around the first electrode and inside the second electrode.

Additionally or alternatively, the body may comprise an inner body member and an outer body member that is adapted to receive the inner body member, the body having an assembled state wherein the inner body member is inside the outer body member, and a detached state wherein the inner and outer body members are separated from each other, the ultrasonic transducer being mounted on at least one among the inner and outer body members.

The tool may further comprise a handle adapted to be gripped by the user's hand and which extends from the body, the handle comprising a housing adapted to receive at least a portion of at least one of the devices among the location measurement device and the location processing device.

The medical system may allow viewing the entry point of the surgical instrument into the first anatomical structure. For this purpose, the medical system may further comprise:
a view measurement device adapted for, at a plurality of sites of a viewing area of the external surface of the second anatomical structure:
emitting at least one ultrasound view signal adapted to propagate in the body part and to be at least partially reflected at the interface between the first and second anatomical structures, and
receiving at least one reflected view signal corresponding to a reflection of a portion of the ultrasound view signal, the reflected view signal being in the form of a plurality of echoes of amplitudes that vary over time,
a view processing device connected to the view measurement device and adapted for, at each site:
detecting, in the reflected view signal, a target view echo corresponding to the interface between the first and second anatomical structures that is next to the viewing area, the target view echo having an amplitude which exceeds a determined viewing threshold,
measuring a time of flight between emission of the ultrasound view signal and detection of the target view echo,
determining a depth at which the interface is located, based on the measured time of flight,
and adapted for representing a portion of the external surface of the first anatomical structure that is next to the viewing area, based on the depths determined for the plurality of sites.
The view processing device may be adapted for:
assigning, to each site, coordinates in a reference system,

defining, at each site, an interface point in the reference system based on the coordinates of the site and on the determined depth, representing in the reference system the portion of the external surface of the first anatomical structure that is next to the viewing area, based on the defined interface points.

The view processing device may comprise a processor adapted to associate each of the measured times of flight with a value of a viewing parameter, such as a color or a contrast, and a display device adapted to represent the external surface of the first anatomical structure by displaying the value of the viewing parameter corresponding to the time of flight measured at each site.

The view measurement device may comprise a support and at least one ultrasonic transducer arranged on the support, the support having an emission-reception surface in contact with the ultrasonic transducer and adapted to emit the ultrasound view signal and to receive the reflected view signal, the emission-reception surface being intended to be placed in contact with the external surface of the second anatomical structure.

In particular, the view measurement device may comprise an array of ultrasonic transducers and the support may comprise an opening which extends between the emission-reception surface and an external surface opposite to the emission-reception surface, the opening being adapted to allow the passage of a portion of the surgical instrument.

To view the entry point of the surgical instrument into a bone structure serving as the first anatomical structure, the body part further comprising a soft tissue structure serving as the second anatomical structure, the view measurement device may be adapted to emit an ultrasonic wave of a frequency between 100 kHz and 10 MHz.

To view the entry point of the surgical instrument having an insertion end and an external surface, the view processing device may be adapted for detecting, in the reflected view signal, an instrument echo corresponding to the external surface of the surgical instrument, the instrument echo having an amplitude which exceeds a defined instrument threshold, measuring a time of flight between emission of the ultrasound view signal and detection of the instrument echo, representing at least a portion of the external surface of the surgical instrument in the vicinity of the insertion end, on the external surface of the first anatomical structure, based on the measured times of flight.

The instrument threshold may be equal to the viewing threshold.

In a second aspect, the invention provides an assembly comprising a medical system as defined above and a surgical instrument adapted to penetrate a first anatomical structure, such as a bone structure, of a body part of a patient.

The body of the tool may be adapted to penetrate the first anatomical structure, the tool forming the surgical instrument.

In a third aspect, the invention provides a method for locating an entry point of a surgical instrument into a first anatomical structure of a body part of a patient, and for identifying a path of the surgical instrument in the first anatomical structure, the body part further comprising a second anatomical structure having a portion that covers the first anatomical structure, the first and second anatomical structures respectively having surfaces in contact defining at least one interface, the first anatomical structure having an external surface, the second anatomical structure having an internal surface in contact with the external surface of the first anatomical structure, and an external surface opposite the first anatomical structure, the first and second anatomical structures respectively having first and second acoustic impedances, the first acoustic impedance being greater than the second acoustic impedance, the method making use of the medical system as defined above and comprising the steps of in at least one site of the external surface of the first anatomical structure, emitting from the distal end of the body an ultrasound location signal adapted to propagate in the first anatomical structure and to be at least partially reflected at the interface between the first and second anatomical structures, and receiving at least one reflected location signal corresponding to a reflection of a portion of the ultrasound location signal, the reflected location signal being in the form of a plurality of echoes of amplitudes that vary over time, at each site, comparing each of the echoes of the reflected location signal to a defined location threshold, emitting an information signal if no target location echo corresponding to the interface between the first and second anatomical structures has been identified within an analysis time window, the target location echo having an amplitude which exceeds the location threshold.

The first anatomical structure may be a bone structure and the second anatomical structure may be a soft tissue structure.

When the medical system allows viewing the entry point of the surgical instrument, the method may further comprise the steps of.

at a plurality of sites in a viewing area of the external surface of the second anatomical structure, emitting at least one ultrasound view signal adapted to propagate in the body part and to be at least partially reflected at the interface between the first and second anatomical structures, and receiving at least one reflected view signal corresponding to a reflection of a portion of the ultrasound view signal, the reflected view signal being in the form of a plurality of echoes of amplitudes that vary over time, at each site, detecting in the reflected view signal, a target view echo corresponding to the interface between the first and second anatomical structures that is next to the viewing area, the target view echo having an amplitude that exceeds a viewing threshold, measuring the time of flight between emission of the ultrasound view signal and detection of the target view echo, and determining a depth at which the interface is located, based on the measured time of flight, representing a portion of the external surface of the first anatomical structure that is next to the viewing area, based on the depths determined for the plurality of sites.

To view the entry point of a surgical instrument having an insertion end and an external surface, the method may further comprise the steps of detecting, in the reflected view signal, an instrument echo corresponding to the external surface of the surgical instrument, the instrument echo having an amplitude which exceeds a defined instrument threshold, measuring a time of flight between emission of the ultrasound view signal and detection of the instrument echo, representing at least a portion of the external surface of the surgical instrument in the vicinity of the insertion end, on the external surface of the first anatomical structure, based on the measured times of flight.

BRIEF DESCRIPTION OF THE DRAWINGS

Other objects and advantages of the invention will be apparent from reading the following description of specific embodiments of the invention given by way of non-limiting example, the description being made with reference to the accompanying drawings in which.

DETAILED DESCRIPTION OF THE DISCLOSURE

In the figures, the same references designate identical or similar elements.

Figure 1:
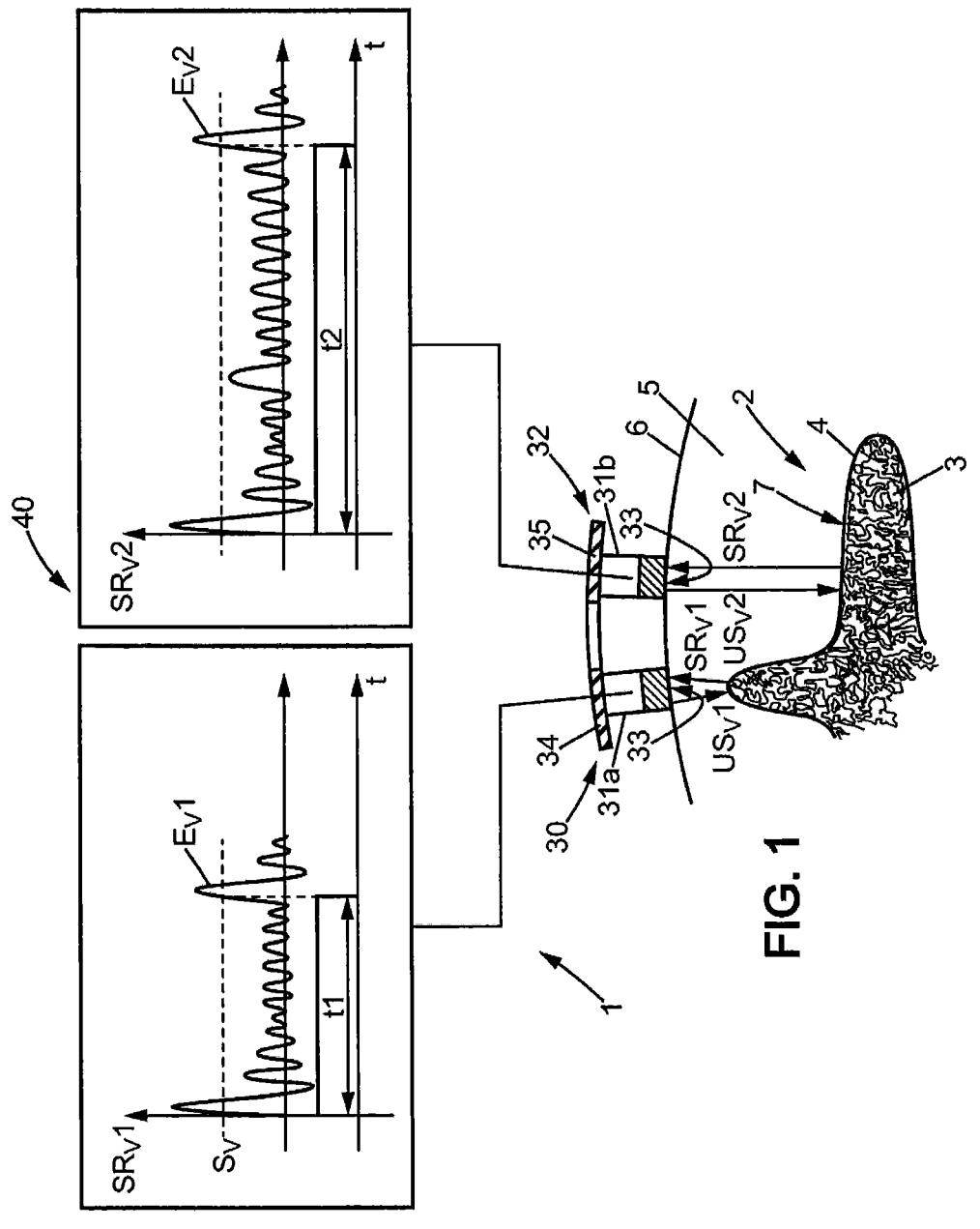
FIG. 1 is a schematic representation of a step of a method for viewing an entry point of a surgical instrument into a first anatomical structure, such as a bone structure, the method making use of a medical system comprising a view measurement device adapted to emit an ultrasound view signal and to receive a reflected view signal corresponding to a reflection of a portion of the ultrasound view signal, and a view processing device adapted to represent a surface of the first anatomical structure based on times of flight measured between emission of the ultrasound view signal and detection of a target view echo of the reflected view signal corresponding to the interface between the first anatomical structure and a second anatomical structure, such as a soft tissue structure, covering the bone structure.

FIG. 1 schematically represents a medical system 1 for determining an entry point of a surgical instrument 10 into a first anatomical structure of a body part of a patient.

In the embodiment represented, the first anatomical structure is a bone structure 3 of a vertebra 2 of the spinal column of a patient. The bone structure 3 has an external surface 4 covered by a second anatomical structure, namely an external soft tissue structure 5 comprising especially muscle, fat, and skin. The external soft tissue structure 5 has an internal surface in contact with the external surface 4 of the bone structure 3, and an external surface 6 opposite the bone structure 3. The external surface 4 of the bone structure 3 and the internal surface of the external soft tissue structure 5 define an external interface 7. The vertebra 2 also encloses an internal soft tissue structure 8, visible in FIGS. 5 to 6, including especially the spinal cord. The bone structure 3 and the internal soft tissue structure 8 therefore also respectively have internal and external contact surfaces defining an internal interface 9.

The invention described in relation to the first and second anatomical structures respectively constituted by a bone structure 3 and external 5 and internal 8 soft tissue structures is not limited, however, to such anatomical structures and may be applied to any type of first and second anatomical structures where the first anatomical structure has a first acoustic impedance greater than a second acoustic impedance of the second anatomical structure.

Figures 3, 4:
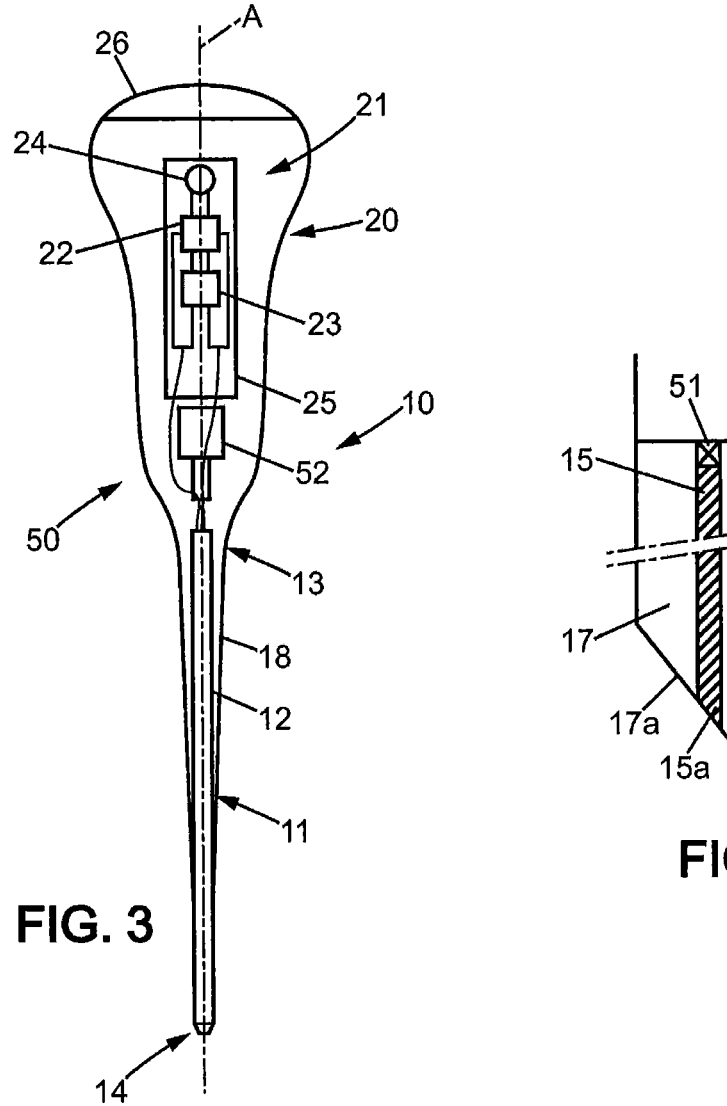
FIG. 3 is a schematic representation of a surgical instrument adapted to penetrate the first anatomical structure, according to a first embodiment of the invention, the surgical instrument forming a tool adapted for locating the entry point and identifying the path of the surgical instrument in the first anatomical structure, the tool comprising a location measurement device adapted to emit an ultrasound location signal and to receive a reflected location signal, and a location processing device adapted to emit an information signal if no second target location echo of the reflected location signal corresponding to the interface between the first and second anatomical structures has been identified after a threshold period of time has elapsed since detection of a first target location echo.
FIG. 4 is a schematic representation of a body of the surgical instrument of FIG. 3, illustrating the arrangement of an ultrasonic transducer at a proximal end of the body and a layer of electrically insulating material placed between first and second electrodes and adapted to transmit the ultrasound location signal and the reflected location signal to an emission-reception surface arranged at a distal end of the body.

In a first embodiment schematically represented in FIGS. 3 and 4, the surgical instrument 10 may be constituted by a hand tool suitable for drilling a bone structure 3, of the type described in patent application WO 03/068076 and marketed under the name PediGuard®. Although described in relation to such a tool, the invention is not limited to this type of surgical instrument. In particular, the invention can be implemented with other types of surgical instruments, notably a probe, an awl, a drill bit, a spatula, a curette, any other tool possibly supported by a robot arm, or an implant such as a screw and in particular a pedicle screw.

The tool 10 comprises a body 11 adapted to penetrate the bone structure 3, and a housing 20 forming a handle secured to the body 11 and adapted to be held by a user's hand. Depending on the application, the housing 20 may also be adapted to be secured to an end of a robot arm.

The body 11, schematically represented in FIG. 4, has an external surface 12 and serves to support first 16 and second 17 electrodes respectively having first 16a and second 17a contact surfaces arranged to come in contact with the bone structure 3 at a distance from one another.

In the embodiment shown, the body 11 is cylindrical along a central axis A with a circular cross-section, and extends from a proximal end 13 secured to the handle 20 to a distal end 14 defining an insertion end. The body 11 could, however, have any other shape, such as cylindrical with a polygonal cross-section or some other shape.

The first electrode 16, cylindrical and of conductive material, extends inside the body 11 parallel to the central axis A. In particular, the first electrode 16 is arranged within a central bore of the body 11 and extends coaxially to the central axis A to a free end providing the first contact surface 16a. The first contact surface 16a is flush with the external surface 12 of the body 11 at its distal end 14. The second electrode 17, annular and of conductive material, extends along the central axis A around the first electrode 16. The second electrode 17 may, in particular, be formed by the body 11 itself, and then is made of a conductive material. The second contact surface 17a of the second electrode 17 is composed of a cylindrical portion parallel to the central axis A, corresponding to a lateral surface of the body 11, and a portion that is transversely annular relative to the central axis A, corresponding to a distal surface of the body 11.

A layer of electrically insulating material 15 is interposed between the first 16 and second 17 electrodes. The layer of electrically insulating material 15 extends along the body 11, from the proximal end 13 of the body 11 to the distal end 14 of the body 11 where it is flush with a free end surface 15a. In the embodiment represented, the annular electrically insulating material layer 15 extends along the central axis A around the first electrode 16 and inside the second electrode 17.

The invention is, however, not limited to the embodiment and arrangement described above for the body 11, the first 16 and second 17 electrodes, and the layer of electrically insulating material 15. More generally, the first 16 and second 17 electrodes are not necessarily arranged coaxially. In particular, these first 16 and second 17 electrodes may each be implemented as a rod of conductive material buried in the body 11. Furthermore, the first electrode 16 and second electrode 17 may each have an contact surface 16a, 17a flush with the lateral surface or distal surface of the body 11. The body 11 may also support two or more than two first electrodes 16 and two or more than two second electrodes 17.

The handle 20, rotationally symmetrical, extends substantially coaxially with the central axis A of the body 11. The handle 20 has a shape which facilitates gripping and manipulating the tool 10. The handle 20 is made of plastic and is integral with a plastic sleeve 18 extending over a portion of the external surface 12 of the body 11.

The handle 20 comprises a housing 21 adapted to receive an electric generator 22, an electric measurement device 23, and a power supply device 24 providing electric power to the electric generator 22 and measurement device 23. The electric generator 22, the electric measurement device 23, and the power supply device 24 are, for example, placed on a circuit board 25 inserted into the housing 21 through an opening provided at an end of the handle 20 opposite the body 11. A removable cap 26 closes the housing 21.

The electric measurement device 23 is adapted to measure an electrical characteristic continuously and in real time, such as impedance or conductance, that is representative of the capacity of an anatomical structure, in particular the bone structure 3, for conducting an electric current between the first 16a and second 17a contact surfaces. Such an electric measurement device 23 connected to an appropriate processing device allows receiving a tissue change in a relative manner, based on a variation of the measured electrical characteristic, or even identifying a tissue in an absolute manner, based on a value of the measured electrical characteristic.

In FIG. 1, the medical system 1 comprises a view measurement device 30 which includes one or more ultrasonic transducers 31 arranged on a support 32 and each adapted to emit one or more ultrasound view signals $US_V$. Each ultrasound view signal $US_V$ is adapted to propagate in the body part and to be at least partially reflected at the external interface 7 between the bone structure 3 and the external soft tissue structure 5. In addition, each ultrasonic transducer 31 is adapted to receive one or more reflected view signals $SR_V$ corresponding to the reflection of a portion of the ultrasound view signal $US_V$ on anatomical structures of different acoustic impedances.

In the particular embodiment represented, each ultrasound view signal $US_V$ is an ultrasonic longitudinal wave, sinusoid or square, of a frequency between 100 kHz and 10 MHz and of the appropriate amplitude. Each ultrasonic transducer 31 can then be connected to an electric generator delivering a peak-to-peak voltage of between 1 V and 10,000 V.

In the particular embodiment represented, but not limited thereto, a plurality of ultrasonic transducers 31, of which two are visible in FIG. 1, are arranged on the support 31 so as to define an emission-reception surface 33 to be placed in contact with the external surface 6 of the external soft tissue structure 5. In FIG. 1, the emission-reception surface 33 is in direct contact with or is constituted by the set of emission-reception surfaces of the ultrasonic transducers 31. The support 32 has an opening 35 which extends between the emission-reception surface 33 and an external surface 34 opposite the emission-reception surface 33 so as to allow, as will be apparent from the following description, the passage of the body 11 of the tool 10.

The emission-reception surface 33 thus makes it possible, at a plurality of sites of the external surface 6 of the external soft tissue structure 5, to:
transmit each ultrasonic wave $US_V$, and
receive each reflected view signal $SR_V$.

As represented in FIG. 1, each reflected view signal $SR_V$ is in the form of a plurality of echoes of amplitudes that vary over time. Indeed, many echoes may appear as the ultrasonic wave $US_V$ travels, because the structures it traverses are not perfectly homogeneous. However, the inhomogeneity is more significant at the external interface 7 between the bone structure 3 and the external soft tissue structure 5, due to the much higher acoustic impedance of the bone structure 3 compared to that of the external soft tissue structure 5. To identify the external interface 7, a corresponding target view echo $E_V$ will therefore be detected.

To process each reflected view signal $SR_V$, the medical system 1 also comprises a view processing device 40 connected to the view measurement device 30. The view processing device 40 comprises an electronic processor adapted to detect, among the set of echoes of the reflected view signal $SR_V$ at each site, the target view echo $E_V$ corresponding to the external interface 7 between the bone structure 3 and the external soft tissue structure 5. To do this, the processor of the view processing device 40 detects the target view echo $E_V$ which has an amplitude greater than a defined viewing threshold $S_V$. The viewing threshold $S_V$ may be adjustable automatically or manually, according to the acoustic impedances of the different anatomical structures traversed and taking into account the attenuation of the ultrasonic wave $US_V$ during its passage through the various anatomical structures and compensating for this attenuation.

The processor of the view processing device 40 is also adapted to measure a time of flight between emission of the ultrasound view signal $US_V$ and detection of the target view echo $E_V$. In particular, the rising edge of the emitted ultrasonic wave $US_V$ activates a clock which will be stopped by the rising edge of the target view echo signal $E_V$. The time of flight so measured reflects the distance between the ultrasonic transducer 31 and the external interface 7 between the bone structure 3 and the external soft tissue structure 5. It thus corresponds to a depth at which the external interface 7 is located relative to the emission-reception surface 33 and, from there, relative to the external surface 6 of the external soft tissue structure 5 from which the measurement is made. This time of flight may be averaged over several measurements to improve accuracy. It is also possible to measure variations in this time of flight (relative measurements).

The time of flight, once measured, can be represented in order to obtain an "anatomical view" of the external interface 7 between the bone structure 3 and the external soft tissue structure 5 and thus obtain a representation with a three-dimensional rendering of the external surface 4 of the bone structure 3 based on the measured times of flight. In particular, the view processing device 40 is adapted to assign coordinates within a reference system to each site. The coordinates may include an abscissa and an ordinate along first and second directions perpendicular to each other in a Cartesian frame of reference, the depth providing a new coordinate in a third direction perpendicular to the first and second directions. From the coordinates of each site and the depth determined at that site, the view processing device 40 can define and register an interface point in the reference system corresponding to the site. The portion of the external surface 4 of the first anatomical structure 3 that is next to a viewing area containing all sites where the measurement has been made can be represented in the reference system based on the set of defined interface points.

In particular, the processor of the view processing device 40 is adapted to associate each of the measured times of flight with a value of a viewing parameter, such as a color or a contrast. The view processing device 40 then also comprises a display device connected to the processor and adapted to represent the external surface 4 of the bone structure 3 by displaying the value of the viewing parameter corresponding to the measured time of flight at each site. Any form of representation with a three-dimensional rendering is possible: color, contrasts, altitude, etc.

A method for viewing the entry point of the surgical instrument 10 implementing the medical system described above is now described in relation to FIG. 1. The method is described in relation to the two represented ultrasonic transducers 31 of the view measurement device 30, it being understood that this method can be applied to a view measurement device 30 comprising more than two ultrasonic transducers 31.

The emission-reception surface 33 of the array of ultrasonic transducers 31 is placed in contact with a viewing area of the patient's skin located near the vertebra 2 to be imaged. At each of the sites of the ultrasonic transducers 31, one or more ultrasonic waves $US_V$ are emitted towards the vertebra. The ultrasonic waves $US_V$ may be emitted in the form of pulses generated at time intervals sufficiently long to avoid overlap between the ultrasonic view signal $US_V$ and the reflected view signal $SR_V$.

Each ultrasonic wave $US_V$ propagates in the body part and encounters inhomogeneities where it is partially reflected, giving rise to echoes returning toward the corresponding ultrasonic transducer 31. The ultrasonic transducer 31 receives them and transmits the corresponding reflected view signal $SR_V$ to the processor of the view processing device 40.

In particular, a first ultrasonic transducer 31a is positioned over a site where the external soft tissue structure 5 has a first thickness. Among the set of echoes received by the first ultrasonic transducer 31a and transmitted to the processor, the processor detects the target view echo $E_V 1$ that exceeds the viewing threshold $S_V$ after a first time of flight t1. A second ultrasonic transducer 31b is positioned over a site where the external soft tissue structure 5 has a second thickness that is greater than the first thickness. Among the set of echoes received by the second ultrasonic transducer 31b and transmitted to the processor, the processor detects the target view echo $E_V 2$ that exceeds the viewing threshold $S_V$ after a second time of flight t2 that is greater than the first time of flight t1. It should be noted that in FIG. 1, the viewing threshold $S_V$ is represented with a constant value, the amplitude of the echoes of the reflected view signal can then be represented with a value adjusted to compensate for possible attenuation of the ultrasonic wave $US_V$ during its passage through the different anatomical structures. Alternatively, the amplitude of the echoes of the reflected view signal could be represented with an actual detected value, the viewing threshold $S_V$ then being represented with an adjusted, decreasing, value to compensate for the possible attenuation of the ultrasonic wave $US_V$ as it travels through the different anatomical structures.

The first and second depths respectively corresponding to the first t1 and second t2 times of flight can then be determined and respectively associated with first and second coordinates in order to define first and second interface points represented on the display device by two distinct values of the viewing parameter.

The array of ultrasonic transducers 31 may be moved to an adjacent viewing area of the patient's skin.

From the representation of the external surface 4 of the bone structure 3 thus obtained, a practitioner can identify the appropriate entry point for applying the insertion end 14 of the body 11 of the surgical instrument 10 and can begin inserting the surgical instrument 10.

To improve the actual positioning of the insertion end 14 at the identified entry point, the view processing device 40 may further be adapted to represent, on the external surface 4 of the bone structure 3, at least a portion of the external surface 12 of the surgical instrument 10 at or near the insertion end 14. This representation of the surgical instrument 10 may be carried out in particular as described above from the times of flight measured between emission of an ultrasound view signal $US_V$ and detection, in the reflected view signal $SR_V$, of an instrument echo $E_i$ corresponding to the external surface of the surgical instrument 10. The instrument echo $E_i$ can be identified as the reflected view signal echo $SR_V$ that exceeds a defined instrument threshold $S_i$, for example equal to the viewing threshold $S_V$. The body 11 may, for example, bear a reference mark identifiable by means of the ultrasound view signal $US_V$ and the reflected view signal $SR_V$. This mark, made for example of a different material than the rest of the body 11, may be placed at the insertion end 14 or on a portion where the arrangement relative to the insertion end 14 is known.

The insertion end 14 of the surgical instrument 10 can thus be placed under the emission-reception surface 33 by inserting the body 11 under the emission-reception surface 33 through the opening 35 or from the exterior of a peripheral edge of the support 32. The insertion end 14 superimposed on the external surface 4 of the bone structure 3 can be viewed on the display device and moved to the identified entry point.

The medical system 1 and method have been described in relation to a view measurement device 30 comprising an array of ultrasonic transducers 31 which are each able to emit, simultaneously or successively, the ultrasound view signal $US_V$ and to receive the reflected view signal $SR_V$ at a plurality of separate sites of the external surface 6 of the external soft tissue structure 5. These provisions allow directly mapping the observed area.

However, the invention is not limited to such a medical system 1 and to such a method.

Alternatively, the view measurement device 30 of the medical system 1 may comprise a single ultrasonic transducer 31 capable of emitting the ultrasound view signal $US_V$ and of receiving the reflected view signal $SR_V$ at a site of the external surface 6 of the external soft tissue structure 5. The ultrasonic transducer 31 can then sweep the external surface 6 of the external soft tissue structure 5 to obtain successive measurements at several separate sites. The emission-reception surface 33 of the support 32 is in direct contact with or is constituted by the emission-reception surface of the ultrasonic transducer 31 itself. With this variant, FIG. 1 could then illustrate two different positions of the same ultrasonic transducer.

Figure 2:
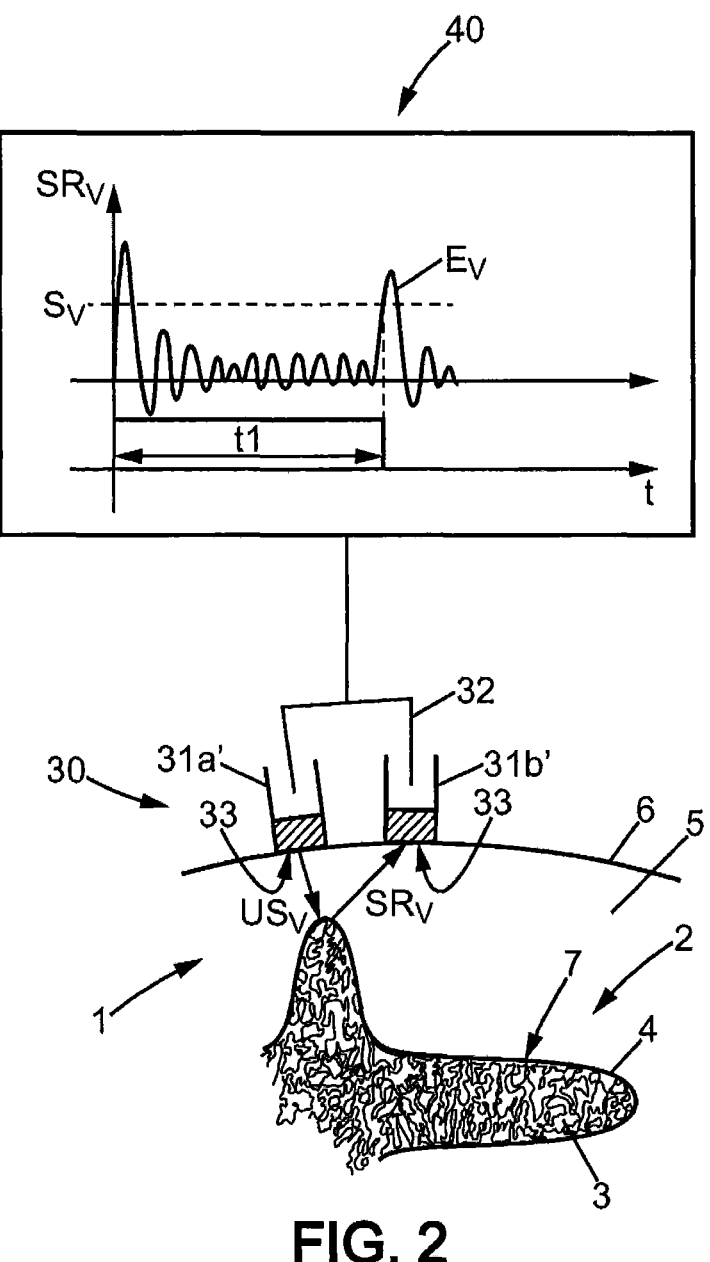
FIG. 2 is a schematic representation of a variant of the medical system of FIG. 1.

According to another variant shown in FIG. 2, the view measurement device 30 of the medical system 1 may comprise one or more pairs of ultrasonic transducers 31, one of the ultrasonic transducers 31a' of each pair being adapted to emit the ultrasound view signal $US_V$ and the other ultrasonic transducer 31b' of each pair being adapted to receive the reflected view signal $SR_V$. The emission-reception surface 33 of the support 32 is in direct contact with or is constituted by a plurality of emission surfaces and a plurality of reception surfaces separated from each other.

In other variants, the emission-reception surface 33 of the support 32 could be a continuous or discontinuous surface in indirect contact, meaning by means of one or more members adapted to transmit an ultrasonic wave, with the emission and/or reception surface of one or more ultrasonic transducers 31 arranged at a distance from the emission-reception surface 33 of the support 32.

Specific provisions concerning the tool 10 described above that enable it to locate the entry point and identify the path of the body in a bone structure 3 will now be described. Although described as complementary to the previous provisions concerning the viewing of the entry point by means of the view measurement device 30 and the view processing device 40, these particular provisions concerning the tool 10 may be provided independently.

In FIGS. 3 and 4, the tool 10 comprises a location measurement device 50 which includes one or more ultrasonic transducers 51 arranged on the body and each adapted to emit one or more ultrasound location signals $US_L$. Each ultrasound location signal $US_L$ is adapted to propagate in the bone structure 3 and to be at least partially reflected at each of the external 7 and internal 9 interfaces between the bone structure 3 and the external 5 and internal 8 soft tissue structures. Each ultrasonic transducer is also adapted to receive one or more reflected location signals $SR_L$ corresponding to a reflection of a portion of the ultrasound location signal $US_L$ on anatomical structures of different acoustic impedances.

In the embodiment represented, each ultrasound location signal $US_L$ is an ultrasonic longitudinal wave, sinusoid or square, with a frequency of between 100 kHz and 10 MHz and of an appropriate amplitude. Each ultrasonic transducer 51 can then be connected to an electric generator 52, for example arranged in the housing 21 of the handle 20, providing a peak-to-peak voltage of between 1 V and 10,000 V.

In the embodiment represented, but not limited thereto, the ultrasonic transducer 51 is arranged at a distance from the distal end, for example near the proximal end 13 of the body 11. The layer of electrically insulating material 15 forms a transmission member adapted to transmit each ultrasound location signal $US_L$ and each reflected location signal $SR_L$. The layer of electrically insulating material 15 is then in contact with the ultrasonic transducer 51 at the proximal end 13 of the body 11 and can successively, via its free end surface 15a forming an emission-reception surface, at one or more sites of the external surface 4 of the bone structure 3:

transmit each ultrasonic wave $US_L$, and receive each reflected location signal $SR_L$.

To do this, the layer of electrically insulating material 15 may be made of any material suitable for electrically insulating the first 16 and second 17 electrodes while having an acoustic impedance adapted to transmit ultrasound, for example ceramic, glass, polymer possibly charged, such as PEEK. The choice of the material and its properties can depend in particular on the geometry of the layer of electrically insulating material 15, the acoustic properties of the ultrasonic transducer 51, and the anatomical structure with which the insertion end 14 of the surgical instrument 10, and in particular the emission-reception surface 15a of the layer of electrically insulating material 15, is in contact.

Although represented with a frustoconical surface, the emission-reception surface 15a may consist of a surface having any other suitable orientation, in particular a planar surface transverse to the central axis A having an orientation along the central axis A that simplifies axially the emission of the ultrasound location signal $US_L$.

Figure 5:
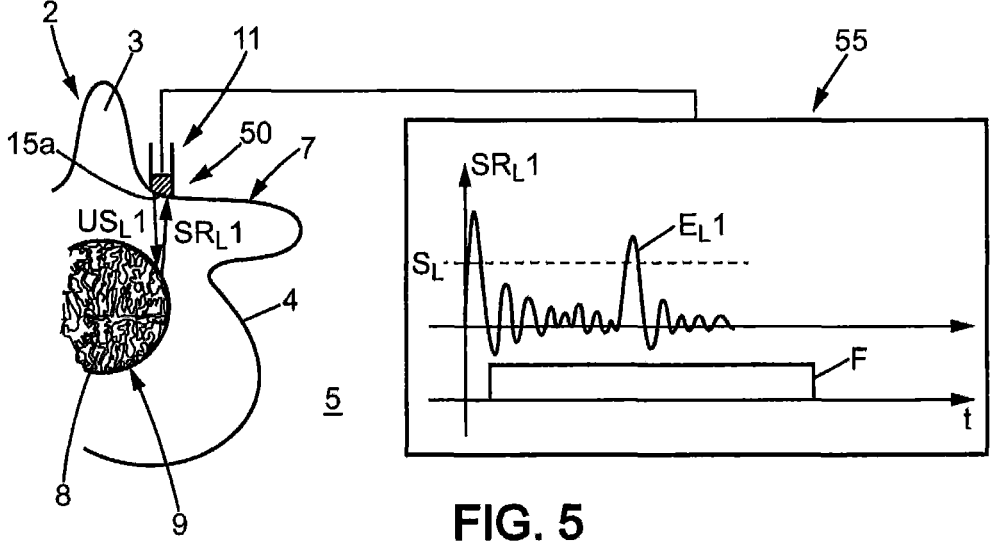
FIGS. 5 to 7 are schematic representations of steps of a method for locating the entry point and identifying the path of the surgical instrument in the first anatomical structure, the method making use of the surgical instrument of FIGS. 3 and 4.
Figure 6:
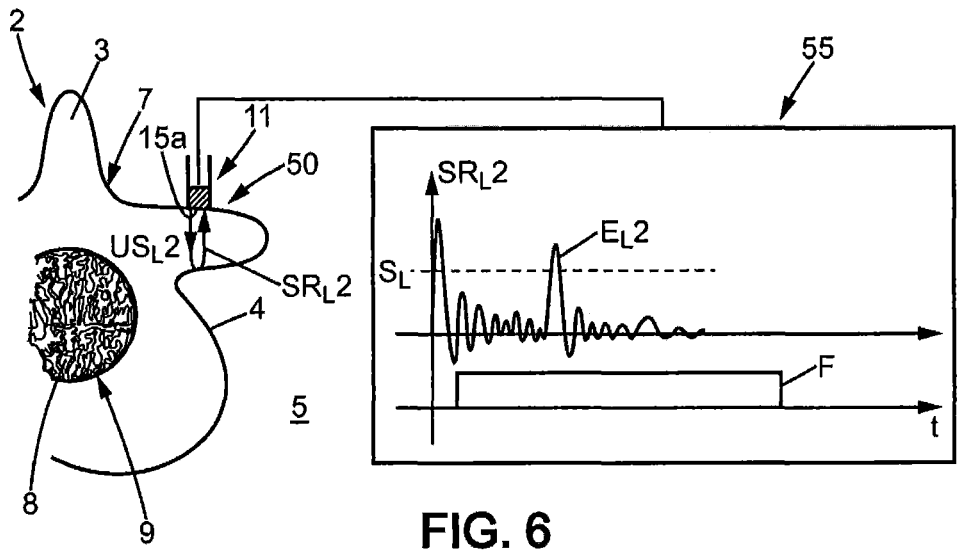
Figure 7:
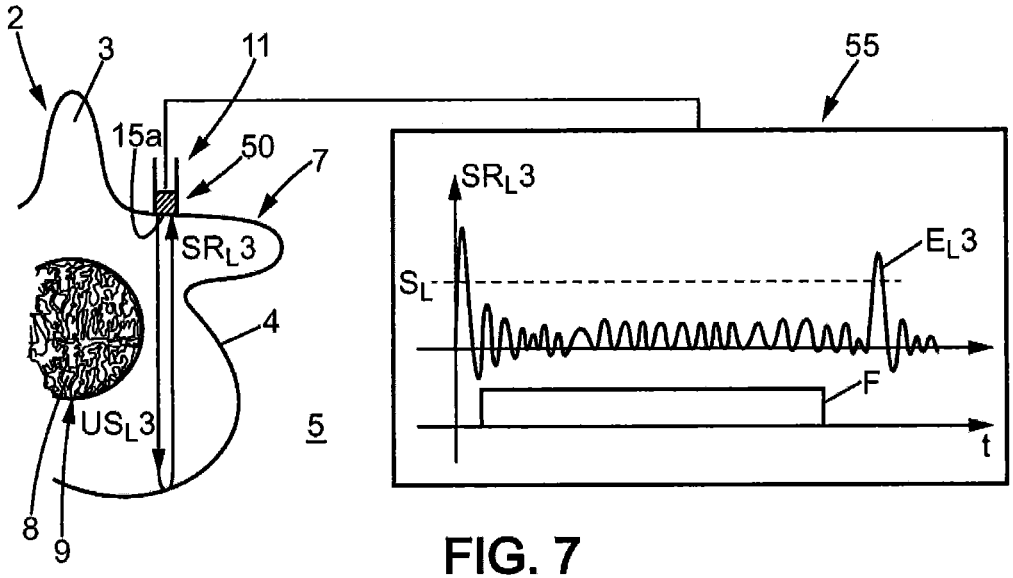

As represented in FIGS. 5 to 7, each reflected location signal $SR_L$ is in the form of a plurality of echoes of amplitudes that vary over time. Indeed, many echoes may appear as the ultrasonic wave $US_L$ travels, because the structures traversed are not perfectly homogeneous.

To process each reflected location signal $SR_L$, the medical system 1 also comprises a location processing device 55 connected to the location measurement device 50. The view processing device 55 comprises an electronic processor adapted to detect, in the set of echoes of the reflected location signal $SR_L$ for each site, the target location echo $E_L$ corresponding to one among the external 7 and internal 9 interfaces between the bone structure 3 and the external 5 and internal 8 soft tissue structures. To do this, the processor of the location processing device 55 detects the target location echo $E_L$ having an amplitude greater than a defined location threshold $S_L$. In effect, the target location echo $E_L$ has a greater amplitude than other echoes due to the greater inhomogeneity at the external 7 and internal 9 interfaces between the bone structure 3 and the external 5 and internal 8 soft tissue structures. In the detection of the target echo location $E_L$, the processor of the location processing device 55 is adapted to take into account adjacent echoes which may have a large amplitude, close to that of the target location echo $E_L$, and in particular an adjacent echo corresponding to an interface between spongy bone and cortical bone within the bone structure. The location threshold $S_L$ may be adjustable automatically or manually according to the acoustic impedances of the different anatomical structures traversed and taking into account the attenuation of the ultrasonic wave $US_L$ as it passes through the various anatomical structures and compensating for this attenuation.

The processor of the location processing device 55 is also adapted to compare each of the echoes of the reflected location signal $SR_L$ to the location threshold $S_L$, and to emit an information signal if no target location echo $E_L$ corresponding to one among the external 7 and internal 9 interfaces between the bone structure 3 and the external 5 and internal 8 soft tissue structures has been identified within an analysis time window F, the target location echo $E_L$ having an amplitude that exceeds the location threshold $S_L$.

The location of the appropriate entry point and the identification of the appropriate path are thus based on the "disappearance", below a certain threshold, the location threshold $S_L$, and within the analysis time window F, of the ultrasound location signals $US_L$. This disappearance is characterized by the absence of echoes representative of one of the external 7 and internal 9 interfaces between the bone structure 3 and the external 5 and internal 8 soft tissue structures, within the analysis time window. This analysis time window F is defined by a starting point and a duration. It may be adjustable according to the size of the bone structure 3 (cervical, thoracic, or lumbar vertebrae) and the quality, in particular the density, of the bone structure 3. The analysis time window F is determined so as to be representative of a thickness in the bone structure 3 which is sufficient to allow insertion of the surgical instrument with no risk of crossing an interface, particularly the interface at the vertebral foramen. Sufficient thickness may depend on the quality, in particular the density, of the bone structure 3. Once determined, the analysis time window F and the location threshold $S_L$ may be stored in memory connected to the processor of the location processing device 55.

The position of the starting point may depend on the characteristics of the ultrasonic transducer 31. This starting point may be the emission of the ultrasound location signal. Alternatively, this starting point may be chosen to avoid the glare due to the emitted ultrasonic wave $US_L$. For example, the starting point may be defined by the falling edge of a first target location echo $E_L$ corresponding to the glare at the external interface 7 between the external surface 4 of the bone structure 3 and the internal surface of the external soft tissue structure 5. The duration may in particular be between 1 μs and 100 μs, which corresponds to a depth of about 3 mm to 150 mm, for example about twenty microseconds. The information signal informing the practitioner of the presence or absence of a target location echo $E_L$ within the analysis time window F may be of any suitable form: oscillogram, contrasting color curves on a display device, sound signal, or some other form.

In relation to FIGS. 5 to 7, a method for locating the entry point of the surgical instrument 10 and identifying the path of the body 11 of the surgical instrument 10 is now described.

The emission-reception surface 15a arranged at the distal end 14 of the body 11 and connected to the ultrasonic transducer 51 is successively placed next to the external surface 4 of the vertebra 2 to be processed, at several sites. At each of the sites where the emission-reception surface 15a is placed, one or more ultrasonic waves $US_L$ are emitted. The ultrasonic waves $US_L$ may be emitted in the form of pulses generated at time intervals sufficiently far apart for there to be no overlap between the ultrasound location signal $US_L$ and the reflected location signal $SR_L$.

Each of the ultrasonic waves $US_L$ propagates in the vertebra 2 and encounters inhomogeneities where it is partially reflected, giving rise to echoes returning toward the emission-reception surface 15a and transmitted to the ultrasonic transducer 51. The ultrasonic transducer 51 receives them and in turn transmits the corresponding reflected location signal $SR_L$ to the processor of the location processing device 55.

In FIG. 5, the emission-reception surface 15a is positioned at a first site next to the vertebral foramen housing the spinal cord 7. Among all the echoes received by the ultrasonic transducer 51 and transmitted to the processor, the processor detects the target location echo $E_L1$ that exceeds the location threshold $S_L$ within the analysis time window F, due to the internal interface 9 between the bone structure 3 and the internal soft tissue structure 8.

Similarly, in FIG. 6, the emission-reception surface 15a positioned at a second site next to one of the transverse spinous processes receives a reflected location signal $SR_L2$ comprising, within the analysis time window F, a target view echo $E_L2$ detected by the processor, due to the external interface 7 between the bone structure 3 and the external soft tissue structure 5 on the external surface 4 of the vertebra 2 opposite the second site.

In contrast, in FIG. 7, the emission-reception surface 15a is positioned at a third site next to one of the vertebral pedicles. The target location echo $E_L3$ of the reflected location signal $SR_L3$ due to the external interface 7 between the bone structure 3 and the external soft tissue structure 5 on the external surface 4 of the vertebra 2 opposite the third site is received outside the analysis time window F. The absence of a target location echo $E_L$ within the analysis time window F and the corresponding information signal indicate to the practitioner that the surgical instrument 10 is aligned with the vertebral pedicle and, therefore, that appropriate entry point and path have been identified.

In FIGS. 5 to 7, as the location threshold $S_L$ is represented with a constant value, the amplitude of the echoes of the reflected location signal can then be represented with a value adjusted to compensate for the possible attenuation of the ultrasonic wave $US_L$ as it travels within the bone structure 3. Alternatively, the amplitude of the echoes of the reflected location signal could be represented with an actual detected value, the location threshold $S_L$ then being represented with an adjusted, decreasing, value to compensate for the possible attenuation of the ultrasonic wave $US_L$ as it travels through the bone structure 3.

The surgical instrument 10 and the method have been described in relation to a single ultrasonic transducer 51 capable of emitting the ultrasound location signal $US_L$ and receiving the reflected location signal $SR_L$, the surgical instrument 10 sweeping the external surface 4 of the bone structure 3 in order to perform successive measurements at a plurality of separate sites.

However, the invention is not limited to such a medical system 1 and to such a method.

In particular, the location measurement device 50 may comprise a plurality of ultrasonic transducers 51, each able to emit, simultaneously or successively, the ultrasound location signal $US_L$ and to receive the reflected location signal $SR_L$ at a plurality of separate sites of the external surface 4 of the bone structure 3.

According to another variant, the location measurement device may comprise one or more pairs of ultrasonic transducers 51, one of the ultrasonic transducers 51 of each pair being adapted to emit the ultrasound location signal $US_L$ and the other ultrasonic transducer of each pair being adapted to receive the reflected location signal $SR_L$.

The surgical instrument could consist of an implant or any other suitable tool.

Figures 8, 9:
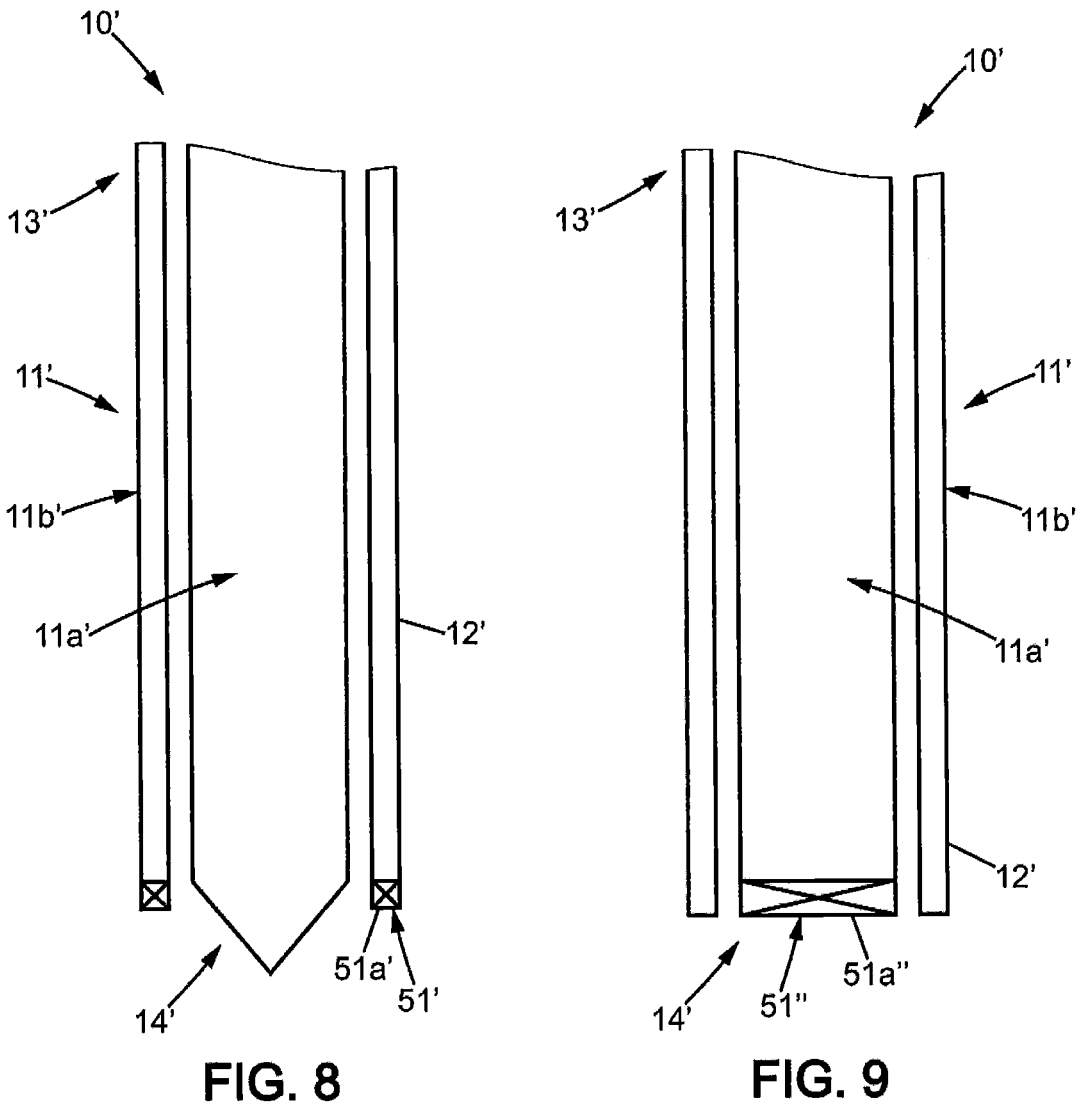
FIG. 8 is a schematic representation of a surgical instrument adapted to penetrate the first anatomical structure, according to a second embodiment of the invention, the surgical instrument forming a tool suitable for locating the entry point and identifying the path of the surgical instrument in the first anatomical structure.
FIG. 9 is a schematic representation of a surgical instrument adapted to penetrate the first anatomical structure, according to a variant of the second embodiment of the invention.

Thus, in a second embodiment schematically represented in FIG. 8, the surgical instrument is a drilling tool 10' comprising a body 11' which has an inner body member 11a' and an outer body member 11b' that is adapted for detachably receiving the inner body member 11a'. Each of the inner body 11a' and outer body 11b' members extends along the central axis A of the body between two ends. In the embodiment represented, the inner body member 11a' is adapted for drilling the bone structure 3.

In FIG. 8, the body 11' is in an assembled state where the inner body member 11a' is inside the outer body member 11b'. The opposite ends of the inner body member 11a' and outer body member 11b' can be correspondingly paired to define the proximal 13' and distal 14' ends of the body 11'. The inner body member 11a' and the outer body member 11b' may be assembled together by any appropriate reversible assembly means, such as press fitting, screwing, or an assembly member, in particular a handle, arranged at the proximal end 13' of the body 11'. In FIG. 8, the inner body member 11a' has an external surface facing an internal surface of the outer body member 11b'. The external surface of the inner body member 11a' is represented as being at a distance from the internal surface of the outer body member 11b', but it is understood that these surfaces may be in contact with each other. By operating the assembly means in an appropriate manner, the body 11' can transition to a detached state where the inner body member 11a' and outer body member 11b' are separated from one another.

In FIG. 8, an ultrasonic transducer 51' is arranged on the outer body member 11b', at the end corresponding to the distal end 14' of the body 11' in the assembled state. The ultrasonic transducer 51' may then have an emission-reception surface 51a' arranged directly at the distal end 14' of the body 11' on the external surface 12' of the body 11'.

In the assembled state of the body 11', the outer body member 11b' is used to locate the appropriate entry point into the bone structure 3 and to determine the appropriate path of the surgical instrument 10', as described above. The inner body member 11a' is then used to drill the bone structure 3 at the appropriate location and orientation. Once a hole has been drilled in the bone structure 3, the inner member 11a' may be removed to leave only the outer body member 11b' which then serves as a guide tube for another surgical instrument.

In a variant illustrated in FIG. 9, an ultrasonic transducer 51" is arranged on the inner body member 11a', at the end corresponding to the distal end 14' of the body 11' in the assembled state. As described above, the inner body member 11a' and outer body member 11b' can be detached from one another once the outer body member 11b' is placed at the appropriate location with the appropriate orientation, so that the outer body member 11b' can serve as a guide tube for another surgical instrument.

In the second embodiment, the transducer 51', 51" may be arranged, as in the first embodiment, at a distance from the distal end 14' of the body 11'. The body 11' may then have a transmission member adapted to transmit the ultrasound location signal $US_L$ and the reflected location signal $SR_L$. The transmission member is then connected to the ultrasonic transducer and extends along the body 11' to an emission-reception surface arranged at the distal end 14' of the body 11' on the external surface 12' of the body 11'.

The surgical instrument suitable for insertion into the guide tube formed by the outer body member 11b' may be the one illustrated in FIG. 3, where appropriate without an ultrasonic transducer specific to it.

Alternatively, the inner body member 11a' and outer body member 11b' may respectively comprise first and second electrodes of the surgical instrument described above.

The invention claimed is:

1. A medical system for locating an entry point of a surgical instrument into a first anatomical structure of a body part of a patient, and for identifying a path of the surgical instrument in the first anatomical structure, the body part further comprising at least one second anatomical structure adjacent to the first anatomical structure and defining at least one interface therebetween, the first anatomical structure having a first acoustic impedance greater than a second acoustic impedance of the at least one second anatomical structure, the medical system comprising a tool comprising:

a body extending along a central axis between opposite proximal and distal ends and having an external surface;

a location measurement device adapted to, in at least one site of an external surface of the first anatomical structure:

emit from the distal end of the body at least one ultrasound location signal adapted to propagate in the first anatomical structure and to be at least partially reflected at the at least one interface between the first anatomical structure and the at least one second anatomical structure; and receive at least one reflected location signal corresponding to a reflection of a portion of the at least one ultrasound location signal, the at least one reflected location signal comprising a plurality of echoes of amplitudes that vary over time;

a location processing device operatively coupled to the location measurement device, the location processing device adapted to:

compare, at each site, each of the echoes of the at least one reflected location signal received by the location measurement device within a predetermined analysis time window to a defined location threshold, the predetermined analysis time window selected based on a thickness of the first anatomical structure; and emit an information signal if no target location echo corresponding to the at least one interface between the first anatomical structure and the at least one second anatomical structure has been identified within the predetermined analysis time window, the target location echo having an amplitude which exceeds the defined location threshold, wherein the first anatomical structure comprises a bone structure and wherein the at least one second anatomical structure comprises a soft tissue structure.

2. The medical system according to claim 1, wherein the predetermined analysis time window is defined by a starting point comprising at least one of the emission of the at least one ultrasound location signal or the detection of a first target location echo, and a duration between 1 μs and 100 μs.

3. The medical system according to claim 1, for locating the entry point and for identifying the path of the surgical instrument in a bone structure serving as the first anatomical structure, the body part further comprising a soft tissue structure serving as the second anatomical structure, wherein the location measurement device is adapted to emit an ultrasonic wave of a frequency between 100 kHz and 10 MHz.

4. The medical system according to claim 1, wherein the location measurement device comprises at least one ultrasonic transducer arranged on the body, the body having an emission-reception surface in contact with the at least one ultrasonic transducer and adapted to emit the at least one ultrasound location signal and to receive the at least one reflected location signal, the emission-reception surface positioned at the distal end of the body on the external surface of the body.

5. The medical system according to claim 4, wherein the at least one ultrasonic transducer is arranged at a distance from the distal end of the body, the body having a transmission member adapted to transmit the at least one ultrasound location signal and the at least one reflected location signal, the transmission member in contact with the at least one ultrasonic transducer and defining the emission-reception surface.

6. The medical system according to claim 5, wherein the tool further comprises:

at least one first electrode having a first contact surface arranged at the distal end of the body on the external surface of the body so as to come into contact with the first anatomical structure;

at least one second electrode having a second contact surface arranged at the distal end of the body on the external surface of the body so as to come into contact with the first anatomical structure at a distance from the first contact surface;

a layer of electrically insulating material interposed between the at least one first and second electrodes; and an electric measurement device adapted to measure continuously and in real time an electrical characteristic representative of the capacity of the first anatomical structure for conducting electric current between the first and second contact surfaces, wherein the layer of electrically insulating material forms the transmission member, and wherein the emission-reception surface is arranged between the first and second contact surfaces.

7. The medical system according to claim 6, wherein the at least one first electrode is cylindrical and extends along the central axis, and the at least one second electrode is annular and extends along the central axis around the at least one first electrode, the layer of electrically insulating material being annular and extending along the central axis around the at least one first electrode and inside the at least one second electrode.

8. The medical system according to claim 4, wherein the body comprises an inner body member and an outer body member that is adapted to receive the inner body member, the body having an assembled state wherein the inner body member is inside the outer body member, and a detached state wherein the inner body member and outer body member are separated from each other, the at least one ultrasonic transducer being mounted on at least one of the inner body member or the outer body member.

9. The medical system according to claim 1, wherein the tool further comprises a handle adapted to be gripped by a user's hand and which extends from the body, the handle comprising a housing adapted to receive at least a portion of at least one of the location measurement device or the location processing device.

10. An assembly comprising:

the medical system according to claim 1; and a surgical instrument adapted to penetrate the first anatomical structure of the body part of the patient, the first anatomical structure comprising a bone structure.

11. The assembly according to claim 10, wherein the body of the tool is adapted to penetrate the first anatomical structure, the tool forming the surgical instrument.

12. A method making use of the medical system according to claim 1 for locating the entry point of the surgical instrument into the first anatomical structure of the body part of the patient, and for identifying the path of the surgical instrument in the first anatomical structure, the method comprising the steps of:

in at least one site of the external surface of the first anatomical structure, emitting from the distal end of the body the at least one ultrasound location signal in the first anatomical structure, and receiving the at least one reflected location signal corresponding to the reflection of the portion of the at least one ultrasound location signal at the at least one interface;

at each site, comparing each of the echoes of the at least one reflected location signal received by the location measurement device within the predetermined analysis time window to the defined location threshold; and emitting the information signal if no target location echo corresponding to the at least one interface between the first anatomical structure and the at least one second anatomical structure has been identified within the predetermined analysis time window.

13. The method according to claim 12, wherein the first anatomical structure is a bone structure and the at least one second anatomical structure is a soft tissue structure.

* * * * *